United States Patent [19]

Vittimberga

[11] Patent Number: 4,976,774
[45] Date of Patent: Dec. 11, 1990

[54] 1-(4'-PYRIDYL)-4-PYRIDONE, ITS DERIVATIVES AND HERBICIDAL USE THEREOF

[75] Inventor: Bruno M. Vittimberga, Kingston, R.I.

[73] Assignee: The Board of Governors for Higher Education, State of Rhode Island and Providence Plantations, Providence, R.I.

[21] Appl. No.: 241,811

[22] Filed: Aug. 2, 1988

Related U.S. Application Data

[63] Continuation of Ser. No. 632,809, Jul. 20, 1984, abandoned.

[51] Int. Cl.$^5$ .................. A01N 43/40; A01N 43/84; C07D 401/04; C07D 413/14
[52] U.S. Cl. .......................... 71/94; 544/107; 544/131; 546/257
[58] Field of Search ............... 546/257; 544/107, 131; 71/94

[56] References Cited

U.S. PATENT DOCUMENTS

| | | | |
|---|---|---|---|
| 1,879,324 | 9/1932 | Koenigs et al. | 546/257 |
| 4,115,101 | 9/1978 | Carlson | 71/94 |
| 4,259,510 | 3/1981 | Johnson | 71/105 |
| 4,474,599 | 10/1984 | Rogers et al. | 71/94 |

FOREIGN PATENT DOCUMENTS

| | | | |
|---|---|---|---|
| 0095152 | 11/1983 | European Pat. Off. | 546/257 |
| 6601804 | 8/1967 | Netherlands | 546/257 |
| 1529439 | 10/1978 | United Kingdom | 71/94 |
| 1577317 | 10/1980 | United Kingdom | 71/94 |

OTHER PUBLICATIONS

Lattrell et al., Chemical Abstracts, vol. 98 (1983) 125762e.
Lattrell et al., Chemical Abstracts, vol. 100 (1984) 6201w.
Morrison, Robert T. and Robert N. Boyd, "Organic Chemistry", 4th Edition (1983) pp. 1173–1174.

*Primary Examiner*—Richard L. Raymond
*Attorney, Agent, or Firm*—Samuels, Gauthier & Stevens

[57] ABSTRACT

Bipyridylium compounds of the formula:

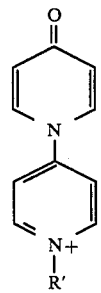

wherein R' has a value known for paraquat and other viologens have been found to have colorimetric and oxidation-reduction properties which make them variously useful as redox indicators, electrochromic display devices, biological mediating agents, and herbicides.

18 Claims, 4 Drawing Sheets

Esr SPECTRUM OF PARAQUAT CATION-RADICAL

Esr SPECTRUM OF THE 1'-METHYL DERIVATIVE OF 1-(4'-PYRIDYL)-4-PYRIDONE

1-(4'-PYRIDYL)-4-PYRIDONE, ITS DERIVATIVES AND HERBICIDAL USE THEREOF

CROSS-REFERENCE TO RELATED APPLICATION

This application is a continuation application of Ser. No. 362,809 filed July 20, 1984 now abandoned.

DESCRIPTION OF THE INVENTION

1. Technical Field of the Invention

This invention relates to compounds having photochemical properties which mimic those of the well-known viologen paraquat and to methods of using them. More particularly, this invention relates to the use of 1-(4'-pyridyl)-4-pyridone and its derivatives as a biological oxidation-reduction indicator and as a non-selective, non-persistent contact herbicide.

2. Background Art

No-till farming, in which farmland is treated with a non-selective herbicide to kill cover crops and weeds which compact down into a layer of protective mulch, holding the soil and providing a seed bed and protection for the crop to come, has resulted in world-wide efforts to replace the plow with herbicides as the standard means for preparing a field for planting. No-till farming takes very little labor, does not disturb the soil, and requires only spraying and planting operations to A wide variety of non-selective herbicides are commonly used in no-till farming including paraquat (the 1,1'-dimethyl-4,4'-bipyridylium cation, normally used as the dichloride salt), described in U.S. Pat. No. 2,972,528 and glyphosate (N-phosphono methylglycine in the form of its isopropyl amine salts) described in U.S. Pat. No. 3,799,531 are among the most widely used. The latter is relatively non-toxic to humans, but suffers the disadvantage of delayed action (up to one week after application) and of being retained in the soil, although it is biodegradable. It contradistinction, paraquat acts often within hours of application on contact with plant material above the soil and is immediately deactivated by clay particles in the soil, thus leaving the soil safe for an emerging crop.

Paradoxically, while paraquat is probably the most effective herbicide currently existing, it is also one of the world's most powerful poisons. While conscientious efforts have been made to reduce the health hazards associated with paraquat, e.g., by the addition of chemically inert odorants, emetics, etc. to the herbicidally effective salt, such attempts are often thwarted when paraquat is handled carelessly or applied by workers in a subsistence and survival economy who feel they cannot afford to take appropriate precautions in handling the material, and in most cases are ineffective in protecting against accidental skin contact, whereby paraquat can be rapidly adsorbed into the human body. A recent article by Andrew C. Revkin on the problems of paraquat toxicity to people taking insufficient care in handling can be found in the June, 1983, issue of Science Digest, pp. 36 ff.

Accordingly, there is still a need for herbicidal compounds which exhibit the activity of paraquat without fully sharing in its toxicity properties.

DISCLOSURE OF THE INVENTION

Accordingly, it is a general object of the present invention to provide a new class of compounds based on 1-(4'pyridyl)-4-pyridone and its derivatives which mimic the electrochemical properties of paraquat and its derivatives.

Another object of the present invention is to provide a series of such compounds which exhibit herbicidal activity.

A further object of the present invention is to provide new methods and compositions for herbicidal treatment of agricultural land in no-till farming.

An additional object of the present invention is to provide a series of stable, reversible colorometric redox indicators.

A more particular object of the present invention is to provide biological redox mediating compounds.

Yet another object of this invention is to provide new compounds for use in electrochemical display devices.

BRIEF DESCRIPTION OF THE DRAWINGS

The above and other objects, features and advantages of the present invention will become more fully apparent to those skilled in the art to which the invention pertains from the following detailed description, taken in conjunction with the annexed drawings, wherein.

BEST MODE FOR CARRYING OUT THE INVENTION

Figure 1A:
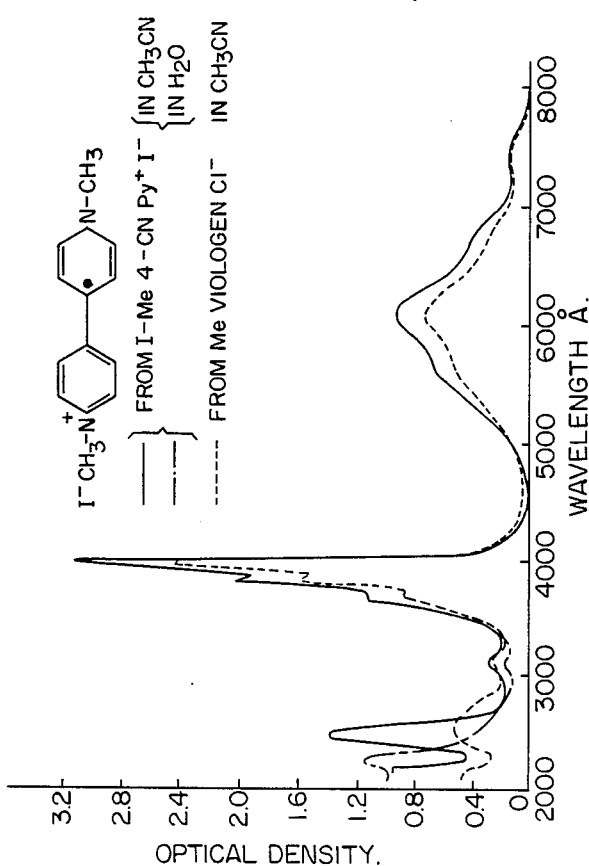
FIGS. 1a and 1b show a representative ultra violet (UV) absorption spectrum of 1-(4'-pyridyl)-4-pyridone shown in comparison with the UV absorption spectrum of paraquat reported by E. Kasower et al. in JACS 86: 5524 (1964)

Briefly, the above and other objects, features and advantages of the present invention are attained in one aspect thereof by providing 1-substituted derbivatives of 1-(4'pyridyl)-4-pyridone having a cationic bipyridylium component of the general Formula 1:

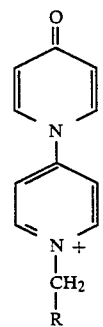

Formula 1 wherein R has the below-indicated values, and their cations, salts, and dimers.

Among the substituents which R can include are hydrogen; alkyl, preferably having up to 4 carbon atoms; aryl, preferably phenyl or substituted phenyl; alkyloxy, preferably having up to 4 carbon atoms; phenoxy or substituted phenoxy; halogen atoms, such as fluorine, chlorine, bromine, and iodine atoms; nitro; perhaloalkyl, such as trifluoromethyl; alkoxyalkyl, preferably having up to 6 carbon atoms; alkoxyalkoxy, preferably having up to 6 carbon atoms; amino, alkyl or dialkyl amino, preferably having up to 4 carbon atoms in each alkyl substituent; cyano; carbalkoxy, preferably having up to 4 carbon atoms in the alkoxy moiety; carbamoyl, alkyl or dialkyl carbamoyl, preferably having up to 4 carbon atoms in each alkyl substituent; sulfo group; sulfonamide; alkylcarbonyl or carboxyalkyl, preferably having up to 4 carbon atoms in the alkyl moiety; alkanoyloxy, preferably having up to 4 carbon atoms; haloalkyl, preferably having up to 4 carbon atoms; alkanoylamido, preferably having up to 4 carbon atoms; alkylthio, preferably having up to 4 carbon atoms; alkylsulfinyl, preferably having up to 4 carbon atoms; alkylsulfonyl, preferably having up to 4 carbon atoms; and the like.

Preferred values for the compounds of Formula 1 are as follows:

(a) hydrogen;
(b) alkyl of 1–20 carbon atoms, especially lower alkyl of 1–4 carbon atoms where herbicidal activity is desired and medium alkyl of 5–12 carbon atoms where insolubility for use in electrochromic displays is desired;
(c) benzyl which may be unsubstituted or substituted, preferably in the p-position, with an electron withdrawing group;
(d) hydroxy or alkoxy of 1–20 carbon atoms, preferably of 1–4 carbon atoms;
(e) halogen or perhaloalkyl, preferably chloride, bromide, iodide, or trifluromethyl;
(f) cyano or cyanoalkyl of 2–6 carbon atoms;
(g) alkanoyl of 2–6 carbon atoms; and
(h) nitro or nitroalkyl (which, however, may interfere with phytoxic properties).

The compounds of this invention provide a useful series of colorimetric oxidation-reduction potential indicators and, characteristic of the "viologens", posses one of the lowest (most cathodic) redox potentials of any organic system showing a significant degree of reversibility. They can be used as redox indicators in biological studies according to techinques first described by T. Michalis and E. S. Hill in J. Gen. Physiol. 16: 859 (1933).

Due to their electrochemically reversible behavior and the marked color change between the two oxidation states, the compounds of this invention are useful in electrochromic display devices, e.g. analagous to the devices described in British Pat. No. 1,514,466. Preferred for most such applications are essentially water-insoluble compounds wherein the R group decreases the water solubility of the parent 1-(4′pyridyl)-4-pyridone, e.g. wherein R is substituted or unsubstituted aryl such as phenyl or benzyl, alkyl of 5–14 carbon atoms, etc., and/or wherein the anion is one which forms solid salts with the 1-(4′-pyridyl)-4-pyridone cation.

The compounds of this invention are also useful as biological mediating compounds which are electrochemically reduced and used to chemically reduce a target compound which cannot be directly reduced electrochemically.

Compounds of this invention may be used in numerous other applications, e.g., in viologen-modified electrodes, battery half cells, the direct conversion of sunlight to electricity, etc., such as have been described by C. L. Bird and A. T. Kuhn in "Electrochemistry of the Viologens", Chem. Soc. Rev. 10: 49–82 (1981), the contents of which are incorporated by reference herein.

Compounds of this invention which have useful phytotoxic properties are those having a half cell potential $E_1$ (NHE electode) of 300–500 mv, preferably about 350–450 mv and especially about 400 mv, since this voltage is effective to shut off the ferritoxin electron transport system in plants. Such a half cell potential $E_1$ is achieved by the presence of electron withdrawing groups on the R substitutent (generally at the first, second or third carbon atom from the pyridone ring in the case of aliphatic substituents and generally in the p-position in the case of aromatic substituents) which are sufficiently strong to lower the half-way reduction potential of the bipyridylium ion to the desired range.

Preferred compounds for use in herbicidal applications can be chosen based on the desired half cell redox potential using several techniques known in the art. For example, using the Hammond correlation one can take a parent pyridyl pyridone compound containing an N-methyl group and prepare various derivatives containing electron withdrawing groups such as hydroxyl, cyano, halo, etc.; using the half cell redox potential plotted against the sigma constant for the electron-withdrawing substituent results in essentially a straight line curve, from which the desired half cell value-substituent combination can be derived. Alternatively, one can plot the sigma constant for various electron-withdrawing substituents as a function of the radical formation rate determined by electron spin resonance, which should give a similar straight line curve.

Based upon the above considerations, preferred herbicidally active compounds according to the present invention are those compounds of 1-(4′pyridyl)-4-pyridone wherein N is substituted with:

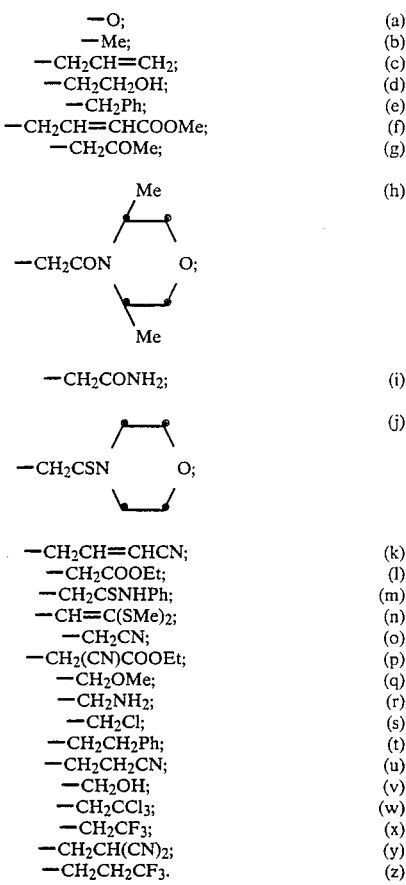

1-(4′Pyridyl)-4-pyridone can be prepared from 4-pyridone and acetic anhydride analogous to the procedure described by F. Arndt and A. Kalischek, Ber. 63B: 587 (1930). This compound serves as a useful starting material for the preparation of its 1-substituted derivatives using techniques which are generally known in the art for the nucleophilic substitution of aromatic amines such as the pyridines, particularly the viologens.

For example compounds of Formula 1 wherein R is alkyl or aralkyl can be prepared by reaction with a suitable alkyl or aralkyl halide, e.g. the chloride, bromide, or iodide, or the corresponding dialkylsulfuric acid or alkylsulfonic acid esters, e.g. dimethyl sulfate, diethyl sulfate, and methyl-p-toluene-sulfonic acid ester. Similarly, compounds of Formula 1 wherein R is allyl can be prepared by reaction with a suitable allyl or arallyl halide, generally in the presence of an acid binding agent such as an alkali metal carbonate, bicarbonate, or hydroxide.

Compounds of this invention which contain a center of asymmetry ordinarily are obtained in the racemic form. The racemates can be separated into their optical antipodes in accordance with a plurality of known methods described in the literature; chemical separation is preferred. According to this procedure, diastereomers are formed from the racemic mixture by reaction with an optically active auxiliary agent. Thus, an optically active base can be reacted with the carboxyl group, or an optically active acid with the amino group, of a compound of this invention. For example, diastereomeric salts of compounds containing a free carboxyl group can be formed with optically active amines, e.g., quinine, cinchonidine, brucine, cinchonine, hydroxyhydrindamine, morphine, 1-phenylethylamine, 1-naphthyl-ethylamine, phenyloxynaphthylmethylamine, quinidine and strychnine, basic amino acids, e.g., lysine, arginine and amino acid esters; or diastereomeric salts of basic compounds can be formed with optically active acids, e.g., (+)- and (−)- tartaric acid, dibenzoyl-(+)- and -(−)-tartaric acid, diacetyl-(+)- and -(−)-tartaric acid, camphoric acid, $\beta$-camphorsulfonic acid, (+)- and (−)-mandelic acid, (+)- and (−)-malic acid, (+)- and (−)-2-phenylbutyric acid, (+)- and (−)-dinitrodiphenic acid, or (+)-and (−)-lactic acid. In a similar manner, ester diastereomers can be produced by the esterification of compounds containing a free carboxyl group with optically active alcohols, e.g., borneol, menthol or 2-octanol. The thus-obtained mixtures of diastereomeric salts and/or esters can be separated by selective crystallization. The desired optically active compounds can be produced by hydrolytic separation of the isolated diastereomeric compound.

Since the herbicidal effect of a bipyridylium quaternary cation is independent of the nature of the associated anion, the choice of the anion is a matter of convenience depending, for example, on cost. Preferably the anion is one which gives rise to a salt of convenient water solubility. Examples of anions, which may be mono- or poly-valent, include acetate, benzenesulphonate, benzoate, bromate, bromide, butyrate, chlorate, chloride, citrate, formate, fluorosilicate, fumarate, fluoroborate, iodate, iodide, lactate, malate, maleate, methylsulphate, nitrate, propionate, phosphate, salicylate, succinate, sulphamate, sulphite, sulphate, thiocynate, tartrate, and p-toluenesulphonate. The salt of the herbicidal bipyridylium cation may be formed from a number of similar anions or mixtures of different ones. A salt having any particular desired anion may be prepared either by direct synthesis from reactants which include the desired anion, or by exchanging the anion of a previously prepared salt for the preferred anion by methods well known in the art, for example by passage of a solution of the previously prepared salt through an ion-exchange resin. For reasons of convenience and economy, the chloride anion is a particularly preferred anion.

Since the characteristic herbicidal activity of a salt of a herbicidal bipyridylium quaternary cation resides in the cation only, it is customary to quote concentrations of active ingredient and rates of application in terms of the amount of bipyridylium quaternary cation used, thus avoiding the inconvenience of having to quote different application rates for different salts of the same bipyridylium quaternary cation. Application rates and concentrations quoted in this specification therefore relate to the amount of herbicidal bipyridylium quaternary cation unless otherwise stated. The amount of herbicidal bipyridylium quaternary cation present in the compositions of the invention is preferably from 50 grams to 300 grams per liter and more preferably from 100 to 250 grams per liter.

The compounds of this invention can be applied in a variety of formulations, including wettable powders, dusts, suspensions, emulsifiable concentrates, solutions, granules, pellets, etc. Concentrates can also be prepared for use by formulators in further processing near the point of use. The formulations will include one or more biocidally active compounds of this invention and can include surface-active agents, solid or liquid diluents and other materials as required to produce the desired formulation.

The surface-active agents act as wetting, dispersing and emulsifying agents which assist dispersion of the active material in the spray, and which improve wetting of waxy foliage and the like by the spray. The surfactants can include such agents as have been used heretofore in similar biocidal compositions. A detailed list of such agents may be found in "Detergents and Emulsifiers Annual," (John W. McCutcheon, Inc.).

Generally speaking, anionic and non-ionic surface-active agents are preferred to cationic surface active agents for use in the herbicidal compositions of the invention, since the latter may interact undesirably with the bipyridylium quaternary salt in the composition. Examples of non-ionic surface agents for use in the compositions of the invention include the condensation products of ethylene oxide with alkyl phenols such as octylphenol, nonylphenol and octylcresol. Other non-ionic agents are the partial esters derived from long chain fatty acids and hexitol anhydrides, for example sorbitan monolaurate; the condensation products of these partial esters with ethylene oxide; and the lecithins. Preferred non-ionic surfactants include alkylphenyl polyethylene glycol ethers, polyoxyethylene derivatives of sorbitan fatty esters and long-chain alcohols and mercaptans, as well as polyoxyethylene esters of fatty acids. The amount of surface-active agent present in the composition is preferably from 20–100 grams per liter of the composition.

Preferred dispersants are alkali and alkaline earth salts of lignosulfonic acids, salts of polymerized alkylarylsulfonates such as are sold under the "Daxad" and "Darvan" trademarks, as well as methylcellulose, polyvinyl alcohol and the like.

Surfactants are present in the compositions of this invention in amounts up to about 20% by weight based on the total weight of the resulting composition. When larger amounts of surfactant are desired, as for improved wetting of, spreading on or penetration into foliage, mixing in the spray tank is usually preferable for convenience.

Powder and dust preparations can be made by blending the active ingredient, with or without surfactant, with finely divided solids such as talcs, natural clays, pyrophyllite, diatomaceous earth; flours such as walnut shell, wheat, redwood, soya bean and cotton seed; or inorganic substances such as magnesium carbonate, calcium carbonate, calcium phosphate, sodium silicoaluminate, sulfur and the like. The choice of a particular diluent is based on consideration of the physical and chemical properties required of the product, the chemical and physical properties and concentration of the active ingredient, and the use for which the formulation is intended. The compositions are made by thoroughly blending the active ingredient with the diluent and other additives. Usually a grinding step, as in a hammer mill or fluid energy mill, is included. The particles in dust and powder preparations are preferably less than 50 microns in average diameter. With compounds which are highly water insoluble, improved activity may be obtained with still finer grinding.

Preferred wettable powder formulations will contain 40% or more active ingredient together with sufficient surfactant and inert diluent to permit dispersion in water for spray application. Compositions intended for dust application will generally contain less than 50% active ingredient.

Powdered compositions can be converted to granules by adding a liquid, treating mechanically, and usually drying. Mechanical devices such as granulating pans, mixers and extruders can be used. Compaction devices can be used even without a liquid in the mixture. Water soluble binders, e.g. inorganic salts, urea, ligninsulfonates, methyl cellulose, other water soluble polymers and the like, can be included in these particulate formulations in amounts up to about 25% by weight of the finished granule or pellet. Such materials also aid in disintegration of the pellet and release of the active ingredient under field conditions. Alternatively, a melt, solution or suspension of the active ingredient can be sprayed on the surfact of preformed granules of clay, vermiculite, corn cob and the like. Surfactants may also be included in formulations of the latter type.

Solution formulations can be prepared in suitable solvents. All solution formulations can be used for direct low-volume applications. For such use, all that is required is practical solubility and stability of the active ingredient in the chosen solvent. An important sub-class of solution formulations is emulsifiable concentrates. For these, a water-immisuble solvent is required as well as surfactant to help form and stabilize the final aqueous emulsion in which the biocide is applied. It is preferred that the active ingredient in solution formulations remain totally dissolved at 0° C. or as low a storage temperature as can reasonably be expected to occur for prolonged periods. In order to insure this, co-solvents, which may be water-miscible, may also be included in the formulations.

Suspension formulations can be made in water, organic solvents or in mixtures of water and water-miscible organic solvents in which the active ingredient has a solubility under about 0.1%. The preparations usually include, in addition to the active ingredient and liquid carrier, surfacts, viscosity control agents and other modifiers. They are prepared by grinding the components in a sand mill, roller mill or pebble mill, preferably until the average particle size is under 20 microns. It is entirely practical, and in some instances biologically advantageous, to grind until a major proportion of active ingredient is 2 microns in diameter or smaller. Hydrocarbon and other flammable carriers should have boiling points above about 125° C. for safety in handling. Suspensions in hydrocarbons are suitable for extension in spray oils and, by inclusion of a suitable emulsifying agent, may also be made sprayable from water.

Organic liquids suitable for preparation of solutions, suspensions and emulsifiable concentrates of the compounds of this invention include alcohols, glycols, Cellosolves, carbitols, ethers, ketones, esters, sulfamides, amides, sulfoxides, sulfones, paraffinic hydrocarbons, aromatic hydrocarbons and halogenated hydrocarbons. Choice of a liquid is dictated by the solubility of the active compound to be used and whether a suspension or solution is desired. The class of compounds represented by the present invention is variable in solubility characteristics, so it is not possible to generalize in the use of particular solvents for particular purposes, although the N-lower alkyl compounds are mostly water soluble.

All compositions intended for spray use can contain minor amounts of additives to reduce foam, inhibit corrosion, prevent claying, reduce caking, etc. as the conditions of use may dictate. The conditions of need for and use of such additives are generally known in the art.

Herbicidal compositions of this invention can contain, in addition to the active ingredient of this invention, conventional insecticides, miticides, bactericides, nematicides, fungicides or other agricultural chemicals such as fertilizer ingredients and the like, so that the compositions can serve useful purposes in addition to the herbicidal activity of the compounds according to this invention.

Preferred rates for application of the compounds of this invention to foliage, stems and fruit of living plants range from 0.01 to $10^3$ kilograms of active ingredient per hectare. More preferred rates are in the range of 0.1 to 100 kilograms per hectare and the most preferred rates are generally in the range of 0.5 to 5 kilograms per hectare. The optimum amount within this range depends upon a number of variables which are well known to those skilled in the art of plant protection. These variables include but are not limited to the plant material to be controlled, weather conditions expected, the type of crop, stage of development of the crop and the interval between applications. Applications within the range given may need to be repeated one or more times at intervals of 1 to 60 days.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Preparation of 1-(4'-Pyridyl)-4-Pyridone

This compound is easily prepared from 4-pyridone and acetic anhydride and serves as a convenient starting material for adding various substituents at the 1-position.

A solution of 4-pyridone (2.0 g, 0.021 moles) and acetic anhydride (3 ml, 0.04 moles) was heated at reflux for 3 hours, forming a brown solution which was allowed to cool slowly to room temperature while the reaction mixture solidified. The solid was washed from the flask with ether and collected on a filter. This material was placed in a Soxhlet extraction thimble and extracted overnight with 500 ml of boiling benzene. The volume of benzene was reduced under vacuum to about 50 ml and then cooled in an ice bath. The crude 1-(4'-pyridyl)-4-pyridone was recrystallized twice from benzene (once with activated charcoal) to give 1.285 g (71% yield) of pure product. The M.P., IR and NMR data were all consistent with the assigned structure.

EXAMPLE 2

Preparation of 1-(1'-Methyl-4'-Pyridyl)-4-Pyridone 1-(4'-pyridyl)-4-pyridone prepared as in Example 1 (1.71 g, 0.01 moles) and iodomethane (2 ml, 0.03 moles) were heated at reflux for one hour. During this time the white pyridone dissolved and a yellow/orange precipitate formed. After one hour the excess iodomethane was removed under vacuum and the remaining solid was recrystallized from ethanol/ether. This gave 2.8 g of light yellow 1-(1'-methyl-4'-pyridinium)-4-pyridone iodide, 90% yield, M.P. 232°-35°). This was converted to the chloride salt by passage through an ion exchange column (Dowex 2-X8) and recrystallized from ethanol/ether to give 1.9 g of product (95% yield), M.P. 228°-32°.

EXAMPLE 3

Preparation of 1-(1'-n-Deryl-4'-Pyridyl)-4-Pyridone 1-(4'-pyridyl)-4-pyridone (0.52 g, 0.003 moles) and 1-bromodecane (2.21 g, 0.01 moles) were heated at reflux for 6 hours. During the course of the reaction the pyridone dissolved and the solution turned slightly brown in color. The reaction was allowed to cool, and then 10 ml of ether was added. This caused a brown oily solid to precipitate. The solvent was decanted and the residue was washed with two 10 ml portions of ether. The brown solid was recrystallized from dioxane/ether to give 0.73 g (62%) of 1-(1'-n-decyl-4'-pyridinium)-4-pyridone bromide.

EXAMPLE 4

Preparation of 1-(1'-p-Bromobenzyl-4-Pyridyl)-4-Pyridone

A solution of 1-(4'-pyridyl)-4-pyridone (0.5 g, 0.003 moles) and p-bromobenzyl bromide (1.5 g, 0.006 moles) in 10 ml of toluene was heated at reflux for 6 hours. After this time there was a brown oil present on the bottom of the flask. The solution was allowed to cool and the solvent was decanted from the flask. The oil was washed twice with ether, whereupon the oil solidified. This solid was recrystallized from acetone by the addition of ether to give 0.57 g of white solid (45% yield), M.P. 166°-168°.

EXAMPLE 5

Reduction Potentials

Reduction potentials were determined for 1-(1'-methyl-4'-pyridinium)-4-pyridone (1-MPP) and for the hydrochloride salt of 1-(4'-pyridyl)-4-pyridone (1-PP). These potentials were determined in 1.0M KCI solution in a pH 6.8 phosphate buffer, using a dropping mercury electrode (DME) and a Ag/AgCl reference electrode. The reduction of these compounds occurs in two separate, one-electron reduction steps. The values (in volts vs. the standard hydrogen electrode) are given below along with those reported for paraquat 2+.

TABLE 1

|  | 1-PP | 1-MPP | Paraquat |
|---|---|---|---|
| 1st | −.878 | −.638 | −.446 |
| 2nd | −1.24 | −.798 | −.798 |

These values show that 1-MPP is somewhat harder to reduce than Paraquat 2+, but the value for 1-MPP is still quite high. There were a number of strange spikes in the polarograms and a plateau was observed at a more negative potential, −1.6V.

EXAMPLE 6

Ease of Radical Formation

Irradiation of 1-(4'-pyridyl)-4-pyridone in the cavity of an ESR spectrometer gave no signal. However, when acid was also present, a colorless radical immediately formed giving a signal similar to that of the blue radical formed from 4,4'-bipyridyl dihydrochloride. The N-methyl derivative formed a blue radical with a spectrum like that of the radical from paraquat 2+.

A $5.5 \times 10^{-4}$ M/L solution of $I_2KI$ was prepared by dissolving iodine (0.0139 g, $5.5 \times 10^{-5}$ moles) and KI (0.0093 g, $5.5 \times 10^{-5}$ moles) in 100 ml of distilled, deionized water. This solution was placed in a Class A buiret attached by an airtight seal to a stirred 50 ml round bottom flask equipped with a nitrogen inlet and outlet port. 25 ml. of a 10 mg./ml. solution of 1-MPP was placed in the round bottom flask and stirred. This solution and the $I_2KI$ solution were both deoxygenated for 45 minutes with nitrogen before the titration. The stream of nitrogen gas was left on through the course of the titration. 4 ml. of the same solution were placed in a large volume UV cell, deoxygenated for the same length of time, and then sealed. Both solutions were irradiated simultaneously for 5 minutes, after which time they were deep blue in color. The radical in the flask was titrated with the $I_2KI$ solution to a yellow endpoint. The solution of radical in the UV cell was used to determine the optical density at 605 nm. From the optical density, and the volume of $I_2KI$ used, the Emax can be calculated. The average of three determinations gave an Emax of 11200.

EXAMPLE 7

Diphenyl Ketyl Electron Transfer

This experiment was conducted to demonstrate electron transfers in the compounds of this invention using a non-photochemical system; the mechanism involves an electron transfer from diphenyl ketyl followed by a substitution.

Figure 1B:
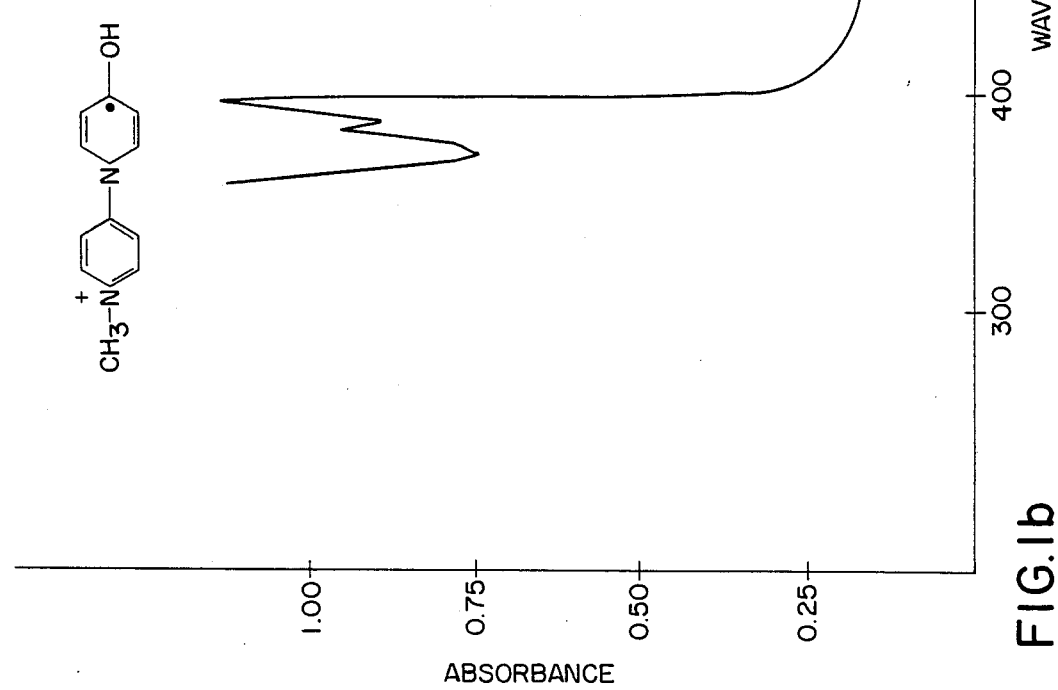
Figure 2:
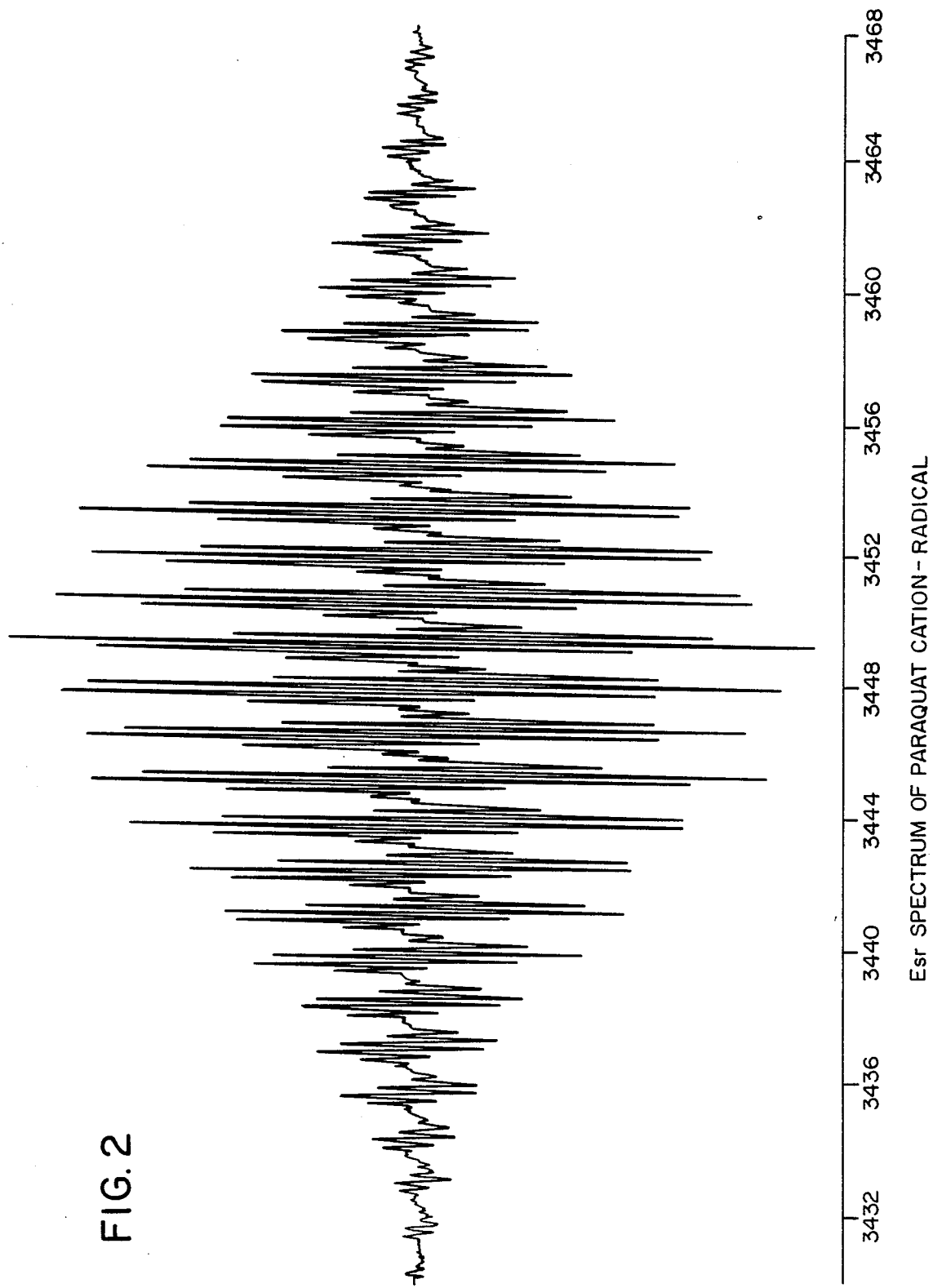
FIG. 2 is a representative electron spin resonance (ESR) spectrum of 1-(4'-pyridyl)-4-pyridone.
Figure 3:
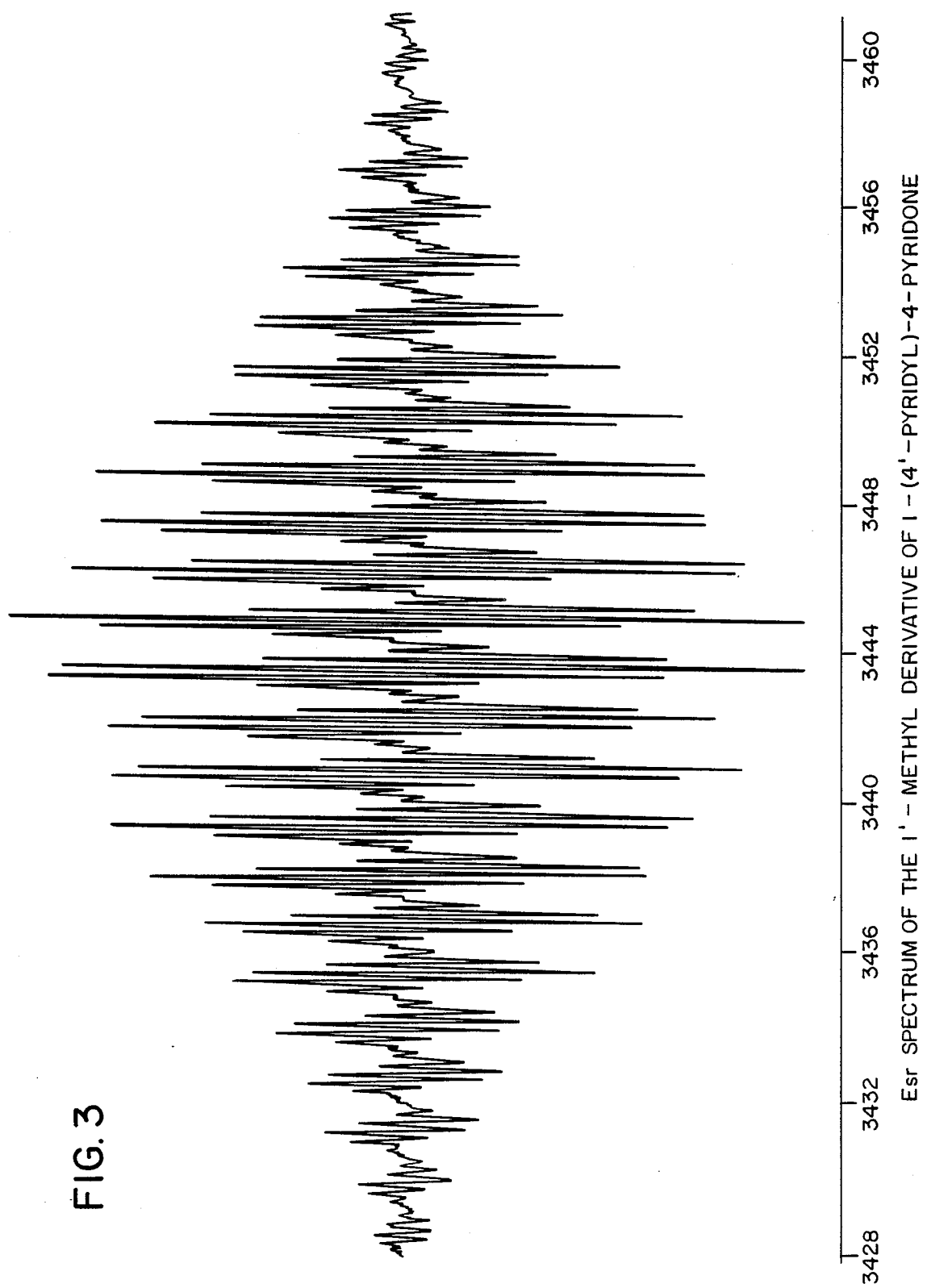
FIG. 3 is an ESR for the known compound paraquat.

A solution of 1-(1'-methyl-4'-pyridyl)-4-pyridone (0.089 g, 0.0004 moles) and benzophinacol (0.073 g, 0.0002 moles) in 5 ml. of 2-propanol/water was placed in a Pyrex test tube (1 cm i.d.) with a constricted neck. This tube was attached to a vacuum system and degassed by three freeze - vacuum - thaw cycles. The tube was then sealed at the constriction while under vacuum and heated to 80° C. in a sand bath, whereupon the blue color of the radical appeared. The tube was then placed in the sample compartment of a Cary 15 UV/VIS spectrometer and the spectrum recorded, using a similar tube with solvent as a reference. The UV/VIS spectrum is shown in FIG. 1.

EXAMPLE 8

Herbicidal Properties of 1-(1'-methyl-4'-Pyridyl)-4-Pyridone 1-(1'-methyl-4'-pyridyl)-4-pyridone was applied as a foliar spray to seedlings of six test plants (corn, barley, pole bean, sunflower, cucumber, and yellow birch) at a rate equivalent to 0.5, 1.0 and 2.0 pounds of active compound per acre in water equivalent to a spray rate of 100 gallons per acre. This was achieved by adding 60, 120 and 240 mg of 1-MPP to 100 ml water spraying 17.4 ml of these solutions over a 2 sq. ft. flat containing the plants. The nonionic surfactant X-77 was added to a concentration of 0.2% (V:V) in order to insure proper foliar contact. As a control, the commercial herbicide paraquat (in the form of its dichloride salt) was similarly applied at a rate of 0.5 pounds per acre. Another control flat was sprayed with 17.4 ml of 0.2% X-77 in water.

Plants were sprayed outside under full late spring sun at 10:30 a.m. and maintained under full sunlight until 4:30 p.m. when the plants were transferred to a greenhouse. The plants were maintained under greenhouse conditions until five days later, when the shoots were harvested and weighed. The plants were photographed and notes on plant appearance were recorded periodically throughout the time between spraying and harvesting.

By 1:00 p.m. on the date of spraying, the paraquat treated plants exhibited distinct injury symptoms to the leaves of all plant species except the yellow birch. At the 2.0 lb. rate, the experimental application caused some leaf darkening of bean and sunflower as if cell membranes had become leaky. By 4:30 p.m. the paraquat control had caused severe leaf injury to all plants while the experimental response was largely unchanged from the earlier observation. During the following four days, the paraquat treated plants continued to decline with all leaves drying and the plants showing clear signs of dying. Only the yellow birch indicated a capacity to survive the paraquat treatment. The experimental compound caused no further injury and the plants exhibited continued growth.

Plant fresh weights recorded five days after spray application are summarized in Table 2.

TABLE 2

Plant Fresh Weights Five Days After Being Sprayed with Photoactive Compounds

| | Herbicidal Treatment | | | |
|---|---|---|---|---|
| | paraquat | 1-(1'-Methyl-4'-Pyridyl)-4-Pyridone | | |
| Plant | control 0.5 lbs/A | 0.5 lbs/A | 1.0 lbs/A | 2.0 lbs/A |
| | grams/Plant* | | | |
| Corn | 5.7  1.4 | 6.0 | 4.8 | 5.8 |
| Barley | 1.1  0.1 | 1.4 | 1.3 | 1.8 |
| Bean | 4.0  0.9 | 4.2 | 3.6 | 3.7 |
| Sunflower | 3.3  0.7 | 2.7 | 3.0 | 3.5 |
| Cucumber | 3.7  0.8 | 3.1 | 3.9 | 3.3 |
| Birch | 0.24  0.17 | 0.28 | 0.20 | 0.24 |

*All values are the mean of beteen 4 to 6 plants.

The experimental compound at the three application rates used exhibited no dramatic phytotoxic properties and did not promote the foliar damage under the full sun that was apparent with paraquat. The failure of this particular compound to exhibit herbicidal properties similar to those of paraquat may be explained by the low reduction potential of the first electron loss: $-0.63_v$ versus $-0.446_v$ for paraquat. The reduction potential of the iron-sulfur center associated with photosystem I is about $-0.550_v$ and normally reduces ferrodoxin with a reduction potential of $-0.42_v$. Thus paraquat (methyl viologen) at $-0.446_v$ can be reduced readily but a compound with a redox potential of $-0.638_v$ is much less likely to gain electrons from this system. Molecular changes in the pyridyl-pyridone structure of the type previously described herein can increase the redox potential to a value closer to that of paraquat and increase its herbicidal activity.

The preceding examples can be repeated with similar success by substituting the generically or specifically described reactants and/or operating conditions of this invention for those specifically used in the examples. From the foregoing description, one skilled in the art to which this invention pertains can easily ascertain the essential characteristics thereof and, without departing from the spirit and scope of the present invention, can make various changes and modifications to adapt it to various usages and conditions.

INDUSTRIAL APPLICABILITY

As can be seen from the foregoing specification and examples, the present invention provides a new class of compounds having colorimetric and oxidation-reduction properties which make them variously useful as redox indicators, electrochromic display devices, biological mediating agents, and herbicides.

What is claimed is:

1. A compound selected from the group consisting of pyridyl pyridones and their salts having a bipyridylium component of the formula

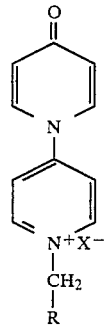

wherein R is selected from the group consisting of hydrogen; alkyl of 1–20 carbons atoms; phenyl; alkyloxy of up to 4 carbon atoms; phenoxy; halogen; nitro; perhaloalkyl; alkoxyalkyl of up to 6 carbon atoms; alkoxyalkoxy of up to 6 carbon atoms; amino, alkyl or dialkyl amino of up to 4 carbon atoms in each alkyl substituent; cyano; carbalkoxy of up to 4 carbon atoms in the alkoxy moiety; carbamoyl, alkyl or dialkyl carbamoyl of up to 4 carbon atoms in each alkyl substituent; sulfo group; sulfonamido; alkylcarbonyl or carboxyalkyl of up to 4 carbon atoms in the alkyl moiety; alkanoyloxy of up to 4 carbon atoms; haloalkyl of up to 4 carbon atoms; alkanoylamido of up to 4 carbon atoms; alkylthio of up to 4 carbon atoms; alkylsulfinyl of up to 4 carbon atoms; and alkylsulfonyl of up to 4 carbon atoms; and wherein R is an electron-withdrawing group which is sufficiently strong to reduce the half-cell potential of said compound and wherein $X^-$ is a mono- or polyvalent anion.

2. A compound according to claim 1, in the form of a salt with one or more monovalent anions.

3. A compound selected from the group consisting of pyridyl pyridones and their salts having a bipyridylium component of the formula

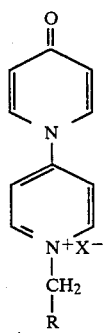

where R is selected from the group consisting of (a) —Me;
(b) —H
(c) —CH=CH$_2$
(d) —CH$_2$OH;
(e) —Ph
(f) —CH=CHCOOMe;
(g) —COMe (h) —CON(Me)(Me)O;

(i) —CONH$_2$;

(j) —CSN O;

(k) —CH=CHCN;
(l) —COOEt;
(m) —CSNHPh;
(n) —CN;
(o) —OMe;
(p) —NH$_2$;
(q) —Cl;

(r) —CH$_2$Ph;

(s) —CH$_2$CN;

(t) —OH;

(u) —CCl$_3$;
(v) —CF$_3$;
(w) —CH(CN)$_2$;
(x) —CH$_2$CF$_3$;

4. A compound according to claim 3, wherein R is —CH=CH$_2$.

5. A compound according to claim 3, wherein R is —CH=CHCOOCH$_3$.

6. A herbicidal composition which comprises a herbicidally effective concentration and amount of a phytotoxic compound according to claim 1 in admixture with a herbicidally acceptable carrier.

7. A composition according to claim 6, wherein said compound has a half cell potential E$_1$ (NHE electrode) of about 350–450 mv.

8. A composition according to claim 7, wherein said compound has a half cell potential of about 420 mv.

9. A herbicidal composition which comprises a herbicidally effective concentration and amount of a phytotoxic compound according to claim 3 in admixture with a herbicidally acceptable carrier.

10. A composition according to claim 9, wherein the compound is one wherein R is —CH=CH$_2$.

11. A composition according to claim 9, wherein the compound is one wherein R is —CH=CHOOCH$_3$.

12. A process for killing unwanted living plants, which comprises contacting the leaves and stems of such plants with a herbicidally effective amount of a phytotoxic compound according to claim 1.

13. A process according to claim 12, wherein said compound is water soluble and is applied in the form of an aqueous solution.

14. A process according to claim 12, wherein said compound has a half cell potential E$_1$ (NHE electrode) of about 350–450 mv.

15. A process according to claim 12, wherein said compound has a half cell potential E$_1$ (NHE electrode) of about 420 mv.

16. A process for killing unwanted living plants, which comprises contacting the leaves and stem of such plants with a herbicidally effective amount of phytotoxic compound according to claim 3.

17. A process according to claim 16, wherein the compound is one wherein R is —CH=CH$_2$.

18. A process according to claim 16, wherein the compound is one wherein R is —CH=CHCOOCH$_3$.

* * * * *

UNITED STATES PATENT AND TRADEMARK OFFICE
CERTIFICATE OF CORRECTION

PATENT NO. : 4,976,774

DATED : Dec. 11, 1990

INVENTOR(S) : Bruno M. Vittimberga

It is certified that error appears in the above—identified patent and that said Letters Patent is hereby corrected as shown below:

Column 1, line 28 after "to" insert -- put in a crop. --

Signed and Sealed this

Eighth Day of June, 1993

Attest:

MICHAEL K. KIRK

Attesting Officer

Acting Commissioner of Patents and Trademarks